(12) United States Patent
Brown et al.

(10) Patent No.: US 9,041,323 B2
(45) Date of Patent: May 26, 2015

(54) APPARATUS AND METHOD FOR ASYMMETRICAL COAST CONTROL OF AN ENDODONTIC MOTOR

(71) Applicant: Ormco Corporation, Orange, CA (US)

(72) Inventors: Erik Brown, Monrovia, CA (US);
Carlos Aloise, Alta Loma, CA (US);
James Shipley, Monroe, WA (US);
Gianluca Gambarini, Rome (IT); Gary Glassman, Toronto (CA); Gary Garman, La Verne, CA (US)

(73) Assignee: Ormco Corporation, Orange, CA (US)

( * ) Notice: Subject to any disclaimer, the term of this patent is extended or adjusted under 35 U.S.C. 154(b) by 214 days.

(21) Appl. No.: 13/786,565

(22) Filed: Mar. 6, 2013

(65) Prior Publication Data
US 2013/0234627 A1    Sep. 12, 2013

Related U.S. Application Data

(60) Provisional application No. 61/608,946, filed on Mar. 9, 2012.

(51) Int. Cl.
*H02P 3/06* (2006.01)
*A61C 5/02* (2006.01)
*A61C 1/00* (2006.01)

(52) U.S. Cl.
CPC ... *H02P 3/06* (2013.01); *A61C 5/02* (2013.01); *A61C 1/003* (2013.01)

(58) Field of Classification Search
CPC ............... H02P 3/06; H02P 3/08; H02P 3/10; H02P 3/22
USPC ......... 318/256, 257, 264, 265, 266, 267, 280, 318/281, 282, 443, 444
See application file for complete search history.

(56) References Cited

U.S. PATENT DOCUMENTS

| 4,142,138 A | 2/1979 | Taylor et al. |
| 4,412,158 A * | 10/1983 | Jefferson et al. ............ 318/257 |

(Continued)

FOREIGN PATENT DOCUMENTS

| EP | 2567671 A1 | 3/2013 |
| JP | S50-3987 | 2/1975 |

(Continued)

OTHER PUBLICATIONS

European Patent Office, Search Report issued in corresponding EP Application No. 13158457.5 dated Jun. 11, 2013, 4 pages.

(Continued)

*Primary Examiner* — Bentsu Ro
(74) *Attorney, Agent, or Firm* — Wood, Herron & Evans, LLP

(57) ABSTRACT

An apparatus for controlling asymmetrical coasting of an endodontic reciprocating motor includes a controller operatively connected to the endodontic motor. The controller may include a processing unit that is configured to direct the rotation of the endodontic motor in the forward direction for a coast time and configured to direct the rotation of the endodontic motor in the reverse direction for a coast time. The forward coast time is separately calculated from the reverse coast time. A method for asymmetrically coasting a reciprocating endodontic motor includes rotating an endodontic motor in a forward direction and calculating a forward coast time for the forward direction and coasting the endodontic motor in the forward direction for the calculated forward coast time. After coasting the endodontic motor in the forward direction, the endodontic motor is rotated in a reverse direction. The reverse coast time is different than the forward coast time.

14 Claims, 3 Drawing Sheets

(56) References Cited

U.S. PATENT DOCUMENTS 4,857,814 A * 8/1989 Duncan .................. 318/281
5,568,026 A * 10/1996 Welch .................... 318/443

FOREIGN PATENT DOCUMENTS

WO      01/03601 A1    1/2001
WO      2010/109464 A2    9/2010

OTHER PUBLICATIONS

Aseptico, Inc., https://web/archive/org/web/20111016000200, Oct. 16, 2011, 1 page.
Japanese Patent Office, Office Action in Japanese Patent Application No. 2013-046422, dated Jan. 26, 2015.

* cited by examiner

APPARATUS AND METHOD FOR ASYMMETRICAL COAST CONTROL OF AN ENDODONTIC MOTOR

CROSS-REFERENCE TO RELATED APPLICATION

This application claims the benefit of U.S. Provisional Patent Application Ser. No. 61/608,946, filed on Mar. 9, 2012, the disclosure of which is expressly incorporated by reference herein in its entirety.

TECHNICAL FIELD

The present invention relates generally to an apparatus and a method for enhancing the performance of an endodontic motor for use during endodontic treatment.

BACKGROUND

Root canal therapy may include clinical instrumentation that is driven by an endodontic motor. Endodontic motors have traditionally been designed to maintain constant rotation of between 300 RPM and 1000 RPM. Typically, a clinician sets the rotation speed. Despite the application of variable torque and friction to the motor during use, constant motor rotation is often maintained by a feedback control loop that dynamically monitors and then acts to maintain the speed of the motor. In this manner, the power output to the endodontic motor varies in accordance with the variable torque and friction observed by the motor to maintain the preset motor speed.

More recently, developments within the endodontic field suggest a performance benefit from a reciprocating endodontic motor. Reciprocating endodontic motors drive the rotor and attached endodontic drill or file through a clockwise rotation and then a counterclockwise rotation. This clockwise-counterclockwise rotation cycle may be repeated very rapidly during treatment. By way of example, the reciprocating endodontic motor may rotate a file clockwise 160 degrees followed by a counterclockwise rotation of 40 degrees. This reciprocating motion may be repeated with any combination of clockwise and counterclockwise rotations of differing degrees to create novel and complex filing cycles. Moreover, by introducing two directions of movement, the attached drill or file has two potentially useful directions, each rotation direction of which is capable of specialization. For instance, a file may be designed for dual use such that it may cut while rotating clockwise, but grind or buff while rotating counterclockwise.

A further modification to the reciprocating endodontic motor is a coast feature. In this regard, at the end of a clockwise or counterclockwise rotation, the motor and attached file will coast under only the influence of its own momentum. For example, an endodontic motor programmed with the coast feature may be programmed to drive a file through a 120 degree clockwise rotation followed by an 80 degree counterclockwise rotation. Following the 120 degree clockwise rotation, the endodontic motor and attached file will continue to rotate, but such rotation will be the result of coasting beyond the specified clockwise rotation. Thus, coasting occurs prior to beginning a counterclockwise rotation of 80 degrees. Regardless of the prescribed angular values, the coast feature permits additional, though unpowered, rotation of the endodontic motor. The amount of such additional rotational coast is dynamically determined and may depend on the time permitted to coast, the angular momentum of the system, and/or the amount of friction encountered by the system. It will be appreciated that generally angular momentum of the motor increases coast time while increased friction reduces coast time.

As applied to reciprocating endodontic motors, the coast feature is a desirable feature because it allows the motor and file to dynamically and automatically respond to various and complex environmental factors, including the specific anatomy encountered during root canal therapy. Rather than the traditional preset and forced control drive which forces a highly prescribed motion, the coast feature allows for greater flexibility of rotational movement. For instance, where the file is spinning freely within the root canal, coast will allow the file to continue spinning while also cutting efficiently to reduce the time to complete the procedure. On the other hand, where the file encounters increased friction due to resistance, coast will decrease the rotation of the endodontic motor to reduce torsional and bending loads applied to the file. In either case, the coast feature provides significant procedural benefits.

Presently, a clinician must choose an amount of coast that is symmetrically applied to the tool. That is, coasting following a clockwise rotation is the same as the coasting following a counterclockwise rotation. Unfortunately, different tools create different frictional forces, which, in turn, affect the amount of optimal coast for a counterclockwise rotation and a clockwise rotation. For instance, a file cutting in the clockwise direction will encounter greater friction and resistance than the same file which produces a buffing action in the counterclockwise direction. Such divergent uses may force a clinician to choose a coast for either cutting or buffing, but not both simultaneously. Thus, a clinician desiring a particular coast in the clockwise direction must also accept this coast in the counterclockwise direction due to the nature of such symmetrical coast control. Identical coast settings are not necessarily advantageous, because significant rotation in the counterclockwise direction may lead to undesirable procedural phenomena such as extrusion of canal debris out of the canal apex, creating post operative pain for the patient.

There is a need for an apparatus and method for use in endodontic procedures, such as root canal therapy, that addresses present challenges and characteristics such as those discussed above.

SUMMARY

The present invention overcomes the foregoing and other shortcomings and drawbacks of endodontic motor control systems heretofore known. While the invention will be described in connection with certain embodiments, it will be understood that the invention is not limited to these embodiments. On the contrary, the invention includes all alternatives, modifications and equivalents as may be included within the spirit and scope of the present invention.

In accordance with the principles of the present invention, an apparatus for controlling asymmetrical coasting of an endodontic reciprocating motor comprises an endodontic motor capable of rotating a tool in a clockwise direction and in a counterclockwise direction. The apparatus further comprises a controller operatively coupled to the endodontic motor. The controller is capable of transmitting electronic signals to the endodontic motor to change the direction of rotation of the tool from the clockwise direction to the counterclockwise direction. The controller is capable of controlling a forward coast time during which the endodontic motor coasts in the clockwise direction and controlling a reverse coast time during which the endodontic motor coasts in the reverse direction. The forward coast time is different from the reverse coast time.

In one embodiment, the controller includes a processing unit operatively connected to the endodontic motor. The processing unit is configured to direct the rotation of the endodontic motor in the forward direction for a forward coast time and configured to direct the rotation of the endodontic motor in the reverse direction for a reverse coast time. The processing unit is configured to calculate the forward coast time separately from the reverse coast time.

In accordance with the principles of the present invention, a method for asymmetrically coasting a reciprocating endodontic motor, comprises rotating an endodontic motor in a forward direction and determining a forward coast time for the forward direction. The method further includes coasting the endodontic motor in the forward direction for the determined forward coast time, and, after coasting the endodontic motor in the forward direction, rotating the endodontic motor in a reverse direction. The method further includes determining a reverse coast time for the reverse direction separately from the determined forward coast time. The reverse coast time is different than the forward coast time. The method further includes coasting the endodontic motor in the reverse direction for the determined reverse coast time.

In one embodiment, determining the forward coast time includes calculating the forward coast time based on a forward coast setting.

In one embodiment, determining the reverse coast time includes calculating the reverse coast time based on a reverse coast setting.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

DETAILED DESCRIPTION

Figure 1:
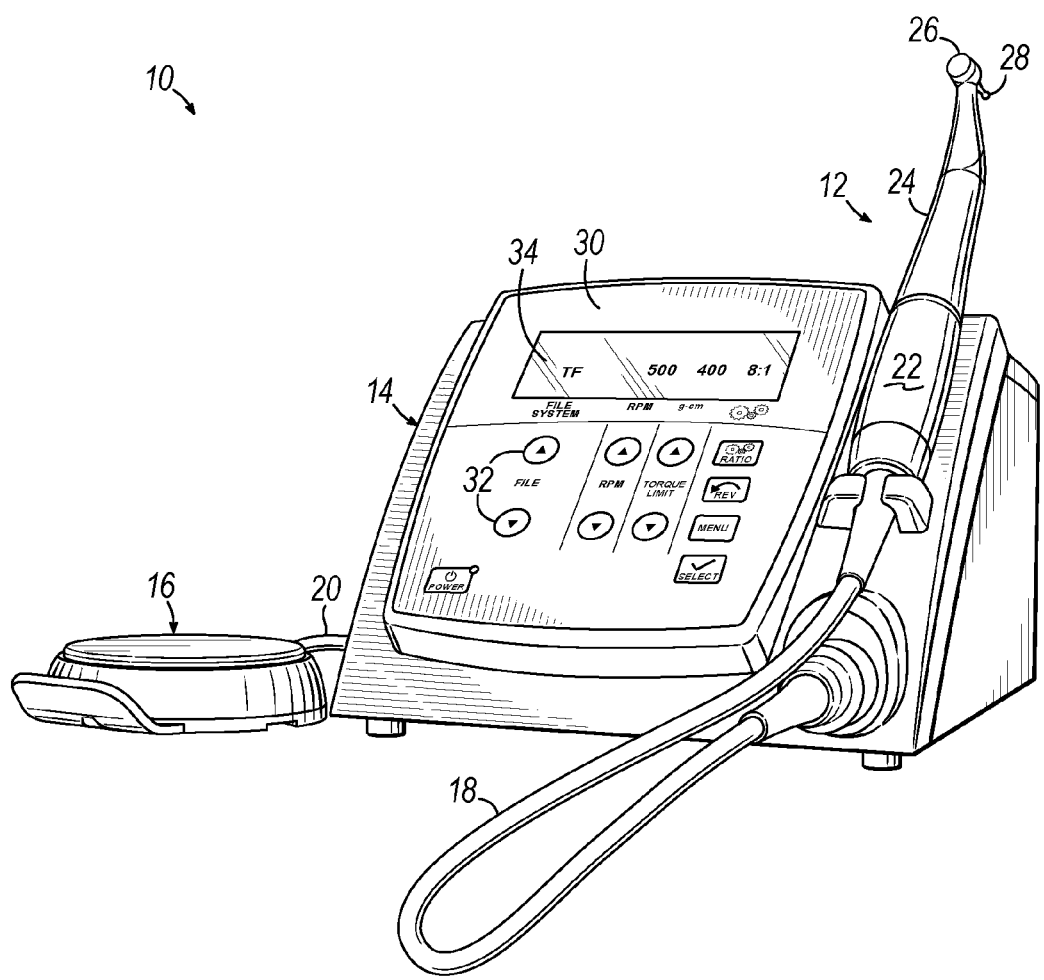
FIG. 1 is a perspective view of one embodiment of an apparatus for controlling asymmetric coasting of an endodontic motor.

With reference to FIG. 1, in one embodiment of the present invention, an apparatus for controlling asymmetric coasting of an endodontic reciprocating motor 10 includes a console 14 and an on/off control switch 16. The console 14 may be operatively coupled to a motor handpiece 12 that is configured to couple to and rotate a tool for use in endodontic treatment. In particular, as is described below, the apparatus 10 is configured to rotate the tool in both the clockwise and counterclockwise directions during a single endodontic operation. The clockwise and counterclockwise rotations may be iteratively repeated over very short periods of time, for example, on the order of seconds or less. The apparatus 10 is also configured to allow the tool to coast in each of the clockwise and counterclockwise directions for a predetermined period of time. This may be referred to as the "coast time" herein. Further, as used herein, the term "coast" means that the rotation of the tool is unpowered. In other words, rotation of the tool is not being forced or acted upon by the apparatus 10. Allowing the tool to coast for a long period of time may result in the tool coming to rest or a complete stop without internal braking of the rotation thereof. By contrast, coasting does not include intentionally reducing the rotation rate of the tool by braking the motor or by other means internal to the apparatus. However, friction inherent in the construction of the handpiece 12 and between the tool and its environment, such as a tooth surface, is contemplated.

In the representative embodiment shown, the motor handpiece 12 is operatively coupled to the console 14 via a cable 18. As is known, the cable 18 may transmit electrical or mechanical power and provide a pathway for electrical feedback from the motor handpiece 12 to the electronics (not shown) housed within the console 14. It will be appreciated that the motor handpiece 12 may not require a cable connection to the console 14, as cordless-type motor handpieces are known in the art. Similarly, the on/off control switch 16, as represented by the foot pedal shown, may be operatively coupled to the console 14 and associated electronics via a power cable 20. A clinician may utilize the control switch 16 to turn the electrical power to the motor handpiece 12 on and off during endodontic treatment.

With continued reference to FIG. 1, in one embodiment, the motor handpiece 12 includes a motor 22 and a gearbox 24 operatively coupled to the motor 22. Motor handpieces that may be coupled to the apparatus 10 are known in the art and include brushless DC motors. As is known, these motors may contain sensors by which the rotor rotation is monitored, for example. The gearbox 24, which may be referred to as a contra angle, may further include a head 26 that is configured to hold an endodontic tool 28, such as, an endodontic file. Energizing the motor 22 causes rotation of a rotor which, in turn, rotates the linkage in the gearbox 22 and ultimately rotates the tool 28 for use in treatment. By way of example, the gearbox 24 may have a gear ratio of 4:1, 8:1, 18:1, or 20:1. Alternatively, the gearbox 24 may have a ratio of 1:10. It will be appreciated that other endodontic tools may be utilized with the apparatus for controlling asymmetrical coasting of an endodontic reciprocating motor 10. Thus, in one embodiment of the invention, the tool 28 is rotated in one direction for a predetermined number of rotations or time, electric power to the motor 22 is shut off or removed, which allows the tool 38 to coast for a predetermined coast time, and, once the predetermined coast time is reached, the tool 28 may be forcibly brought to a stop by braking. Once the brakes are applied, the coast ends. The direction of the tool 28 is then reversed though, according to embodiments of the present invention, the predetermined coast time for the reverse direction is different. According to embodiments of the present invention, the coast time following a clockwise rotation of the tool 28 is separately controlled from the coast time for a counterclockwise rotation of the tool 28.

As introduced above, in one embodiment, the apparatus 10 is configured to rotate the tool 28 in a clockwise direction and is also configured to rotate the tool 28 in a counterclockwise direction. While the clockwise direction may be referred to herein as the forward direction and the counterclockwise direction may be referred to as the reverse direction, such reference is merely for the convenience of description and embodiments of the present invention are not limited to any specific association between forward or reverse and clockwise or counterclockwise.

In the representative embodiment shown, the apparatus 10 includes a control panel 30 by which a clinician may select an operating mode of the apparatus 10. In this regard, the control panel 30 may include numerous pushbuttons 32 by which the clinician can set parameters that ultimately control the rotation of the tool 28. Once selected, an individual parameter may be displayed on screen 34. Of the available parameters, it will be appreciated that the apparatus 10 may be operated in a clockwise rotation mode, a counterclockwise rotation mode, or a reciprocating mode. In one embodiment, in the reciprocating mode, control of the coast time in the forward direction is separate from the control of the coast time in the reverse direction. Thus, in one embodiment the forward coast time is different from the reversed coast time, as is described more fully below.

In particular, and in one embodiment of the present invention, the clinician may select a reciprocating mode for operation of the motor 22 during endodontic treatment. The reciprocating mode includes coasting of the tool in the forward and reverse directions. The coast time in each direction may be asymmetric or different. In this regard, the term "asymmetric" refers to the capability of the apparatus 10 to allow the tool 28 to coast for a preset period of time when rotated in the clockwise direction and/or to allow the tool 28 to coast for a preset period of time when rotated in the counterclockwise direction. The apparatus 10 may thus include independently selectable parameters for each of the clockwise coast and the counterclockwise coast.

Figure 2:
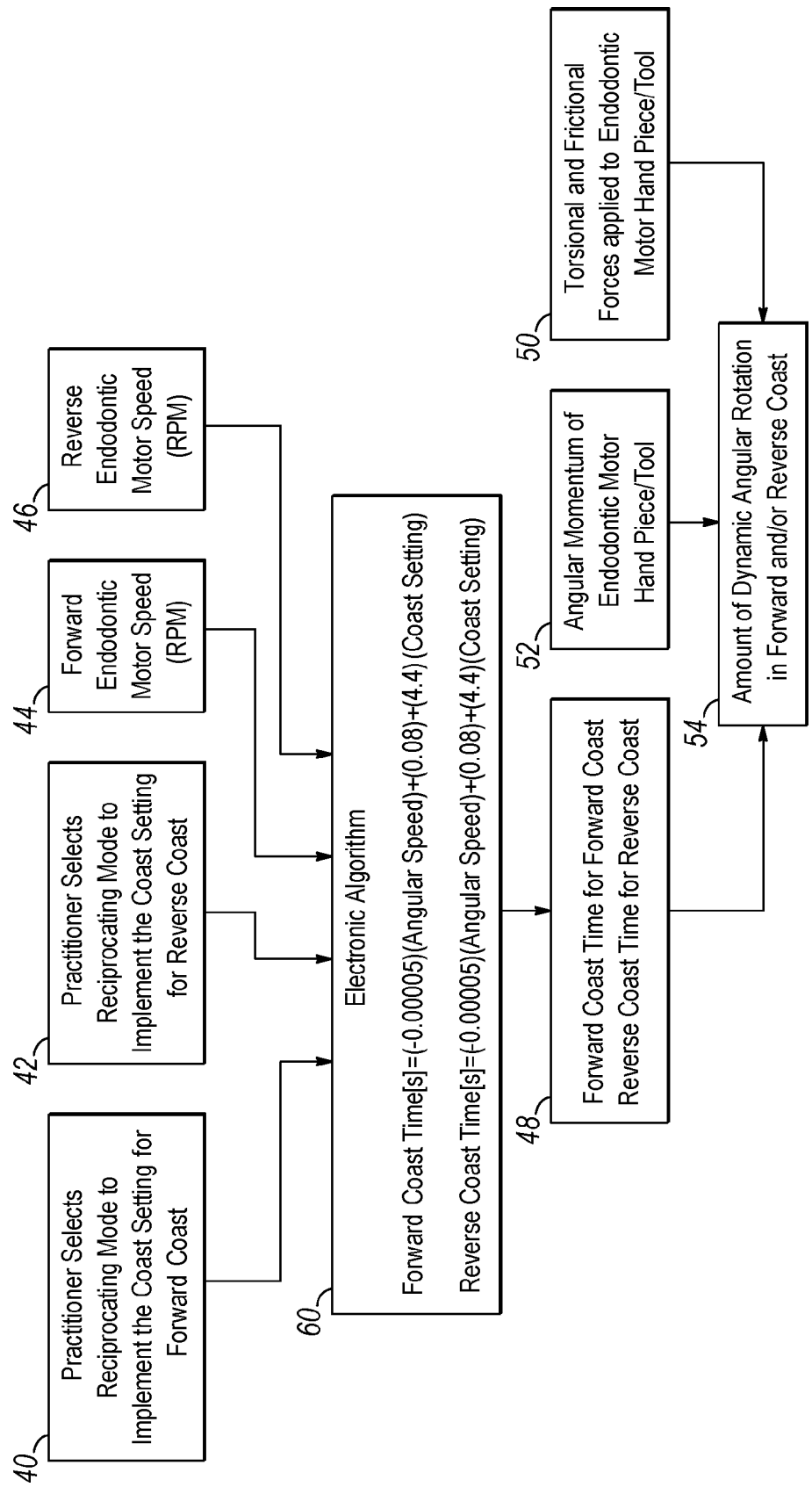
FIG. 2 is a flow chart of one embodiment of a method for asymmetrically coasting a reciprocating endodontic motor according to another aspect of the present invention.

In one embodiment and with reference to FIG. 2, once the reciprocating mode is selected, the clinician may select, via the pushbuttons 32 (FIG. 1), a desired coast setting for coast in the forward direction, i.e., "Forward Coast," at 40. The clinician may, in addition or alternatively, select (via pushbuttons 32) a desired coast setting for the coast in the reverse direction, i.e., "Reverse Coast," at 42. The clinician may also independently select a forward motor speed for the endodontic motor 22 and/or a reverse motor speed for the endodontic motor 22 at 44 and 46, respectively.

Once the clinician selects the desired parameters, as described above, the apparatus 10 calculates the forward coast time for the forward coast and/or the reversed coast time for the reverse coast at 60. The resulting forward coast time and/or reverse coast time as indicated at 48 are utilized to control coasting of the tool 28 during endodontic treatment. Other factors that may be used by the apparatus 10 to control the coasting of the tool 28 may include the angular momentum of the endodontic motor 22 at 52 and/or torsional and frictional forces applied to the endodontic motor 22 at 50. As is noted in FIG. 2, in one embodiment, the apparatus 10 may ultimately calculate the amount of dynamic angular rotation in one or both of the forward and reverse coasts, as is indicated at 54.

As noted above, the clinician may select a coast setting for each of the forward coast and the reverse coast. In general, the coast setting may affect the time that the tool 28 coasts in a given direction. In one embodiment, the desired coast setting for the forward direction is directly related to or is numerically scaled to the amount of coast time observed by the tool 28 in the forward direction. In other words, if the clinician desires more coast time in a particular rotation direction, the clinician may simply set a relatively greater coast setting, for example, by activating a pushbutton 32, for that direction. Similarly, the desired coast setting for the reverse direction may be directly related to or be numerically scaled to the amount of coast time observed by the tool 28 when rotating in the reverse direction. In this sense, the clinician may independently select a coast setting for each of the forward and reverse directions that is optimal for a particular tool. It will be appreciated that the selection may be based upon the clinician's experience with a particular tool, the treatment desired, the patient's anatomy, among other factors. Ultimately, the selected parameters affect the amount of dynamic angular rotation during one or both of the forward and/or reverse coasts as is indicated at 54.

In one embodiment, the coast setting is numerically scaled to increase or decrease the amount of time the endodontic motor allows for one or both of the forward and reverse coasts of the tool 28. Thus, by increasing the coast setting, the permitted dynamic angular travel is increased or, by decreasing the coast setting, the permitted dynamic angular travel is decreased. By way of example only and without limitation, the numerical scale may include predetermined from values of −7 to +7. In this case, −7 may provide for the least amount of coast time, and +7 may provide for the most coast time. By way of further example, a setting of −7 may equate to a coast time range from 0 milliseconds to 24 milliseconds and a setting of +7 may equate to a coast time range from 60 milliseconds to 90 milliseconds. Coast settings of from −7 to +7 may fall approximately between the range of 0 milliseconds to 90 milliseconds in accordance with one embodiment of the electronic control algorithm.

In one embodiment, while the apparatus 10 may provide the controls to vary the coast time for both forward and reverse directions per a coast setting, as described above, the available parameters are not limited to the coast setting. Rather, with reference to FIG. 2, the apparatus 10 may include additional parameters by which the endodontic motor 22 may be operatively controlled to account for applied torque and friction at 50 and/or angular momentum of the handpiece/tool at 52. Such additional metrics may be beneficial to promote greater procedural efficiency as well as to improve the effective life of the endodontic motor 22 and/or the tool 28.

Figure 1A:
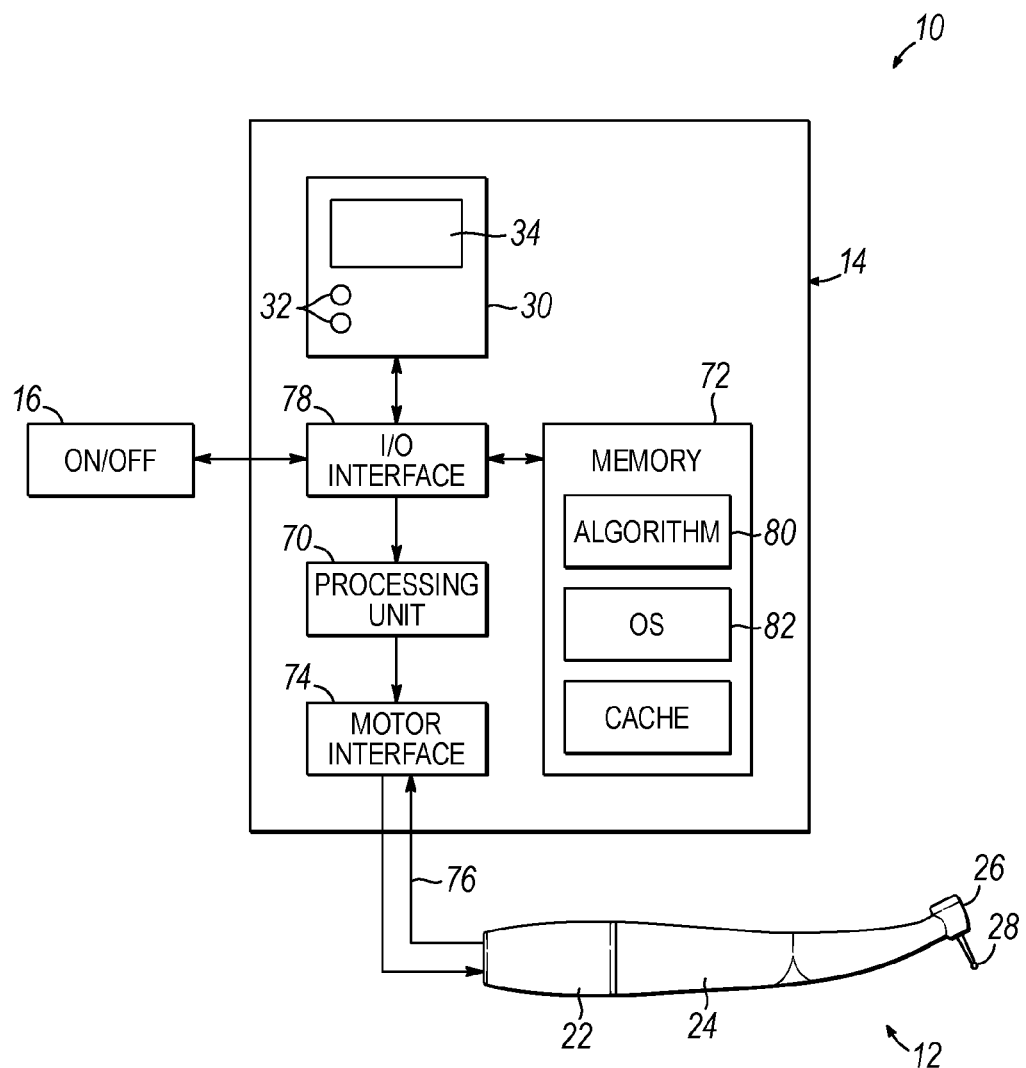
FIG. 1A is a block diagram of the apparatus of FIG. 1.

In one embodiment, and with reference to FIG. 1A, the apparatus for controlling asymmetrical coasting of an endodontic reciprocating motor 10 includes a controller, which in the representative embodiment is a CPU or a processing unit 70, a memory 72, a motor interface 74, and input/output ("I/O") interface 78. The I/O interface 78 may be configured to receive data or signals from the control panel 30, and in particular the pushbuttons 32, and from the on-off control switch 16 that are then communicated to the processing unit 70. The I/O interface 78 may be configured to output data from the processing unit 70 to the control panel 30, and in particular, to the display 34. Though not shown, other devices external to the housing may include additional user input devices such as a keyboard, a keypad, a mouse, a microphone, etc. Embodiments of the present invention are not limited to the external devices shown. The memory 72 is configured to store a software module or an application 80, such as, an electronic control algorithm, as described below, and an operating system 82. The application 80 and operating system 82 each generally comprise one or more instructions stored as program code that may be read from the memory 72 by the processing unit 70. The instructions, when executed by the processing unit 70, may cause the processing unit 70 to perform one or more operations or calculations to thereby perform the steps necessary to execute steps, elements, and/or blocks according to various embodiments of the invention. The memory 72 may represent random-access memory (RAM) comprising the main storage of a computer, as well as any supplemental levels of memory, e.g., cache memories, non-volatile backup memories (e.g., programmable or flash memories), mass storage memory, read-only memories (ROM), etc.

The coast setting is operatively implemented via the processing unit 70 of apparatus 10. In this regard, the apparatus 10 may include various pre-programmed operating modes that include predetermined asymmetric coast times. The modes may be stored in the memory 72 that is accessible by the processing unit 70. Advantageously, the pre-programmed operating modes may include specific parameters for the coast time and the rotation rate for each of the forward and reverse rotation directions. These specific predetermined parameters may be based on prior experience with a particular tool, a particular motor, and/or a particular treatment. In one embodiment, the pre-programmed operating modes preclude any changes to either the forward or reverse coast setting by the clinician. Thus, at least the forward coast setting and the reverse coast setting for a particular pre-programmed operating mode are factory settings.

Furthermore, it will be appreciated that while the apparatus 10 includes a process unit 70 and other components for controlling the coast of the tool, one of ordinary skill will observe that the controller, which may not be the processing unit 70, determines the coast of the tool according to embodiments of the present invention. The controller may include fixed hardware and electrical timing circuits capable of controlling the forward coast time and the reverse coast time. In this embodiment, the forward and the reverse coast time may not be adjustable or selectable. Rather, these times are factory settings, similar to that set out above. Embodiments of the present invention are therefore not limited to the use of a processing unit, though use of fixed hardware would generally preclude software control and would thus make adjustments to the coast setting substantially more complex.

In view of the apparatus 10 described above, a clinician, who has selected a particular tool for a particular endodontic procedure may simply select, via the pushbuttons 32, the desired operating mode that includes all of the optimum parameters for that tool and procedure, for example. Therefore, once the preprogrammed operating mode is selected, the processing unit 70 automatically loads the pre-determined values for the coast setting with respect to a desired coast time for one or both of the forward and reverse directions. The processing unit 70 may then provide one or more signals to the motor interface 74 that then controls the rotation of the motor 22 by regulating the power to the motor 22 according to the one or more signals from the processing unit 70. The apparatus 10 may further include a feedback loop 76 by which rotation of the rotor of the motor 22 may be monitored by the motor controller 74 and/or the processing unit 70, according to known methods in the art. Feedback electrical signals from the motor 22 may be processed by the processing unit 70 and/or the motor interface 74 according to the loop 76 so that the processing unit 70 and/or the motor interface 74 may change the control signal or power to the motor 22 to make adjustments to the rotation of the tool 28.

In one embodiment, the apparatus 10 includes an electronic control algorithm 80. In particular, the electronic control algorithm 80 may be stored in the memory 72 and when the clinician desires control of the forward coast time and/or the reverse coast time by the processing unit 70, the control algorithm 80 may accessed and utilized by the processing unit 70. In one embodiment, and with reference to FIG. 2, the processing unit 70 calculates the forward coast time and/or the reverse coast time via the electronic algorithm at 60. As shown, this calculation may include various parameters, including the coast setting at 40 and 42 and the angular speed for one or both of the forward and reverse directions at 44 and 46. The output from this calculation is the forward coast time for the forward coast and the reverse coast time for the reverse coast, as is indicated at 48.

With continued reference to FIG. 2, a representative electronic control algorithm for controlling a reciprocating endodontic motor is shown at 60. The electronic control algorithm may provide the necessary output to cause the endodontic motor to rotate for a predetermined amount of coast time in one or both of the forward and reverse directions. As shown, the electronic control algorithm calculates the forward coast time and reverse coast time via the preset algorithm:

Forward Coast Time [sec]=(−0.00005)(Forward Angular Speed)+(0.08)+(0.0044)(Forward Coast Setting)

and

Reverse Coast Time [sec]=(−0.00005)(Reverse Angular Speed)+(0.08)+(0.0044)(reverse Coast Setting).

By so doing, the dynamic advantages of coasting are more effectively implemented within a reciprocating endodontic motor.

The program code embodied in any of the applications described herein is capable of being distributed as a computer program product of various different forms. In particular, the program code may be distributed using computer readable storage media. Computer readable storage media are inherently non-transitory, and may include volatile and non-volatile, and removable and non-removable tangible media implemented in any manner. Computer readable storage media may further include random access memory, read-only memory, erasable programmable read-only memory, electrically erasable programmable read-only memory, flash memory or other solid state memory technology, portable compact disc read-only memory, or other optical storage, magnetic cassettes, magnetic tape, magnetic disk storage or other magnetic storage devices, or any other medium that can be used to store the desired information and that can be read by a computer. The program code may also be distributed using communication media, which may embody computer readable instructions, data structures, or other program modules. Communication media may include wired and wireless media.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative apparatus and method and illustrative examples shown and described. Accordingly, departures may be made from such details without departing from the scope or spirit of the general inventive concept.

What is claimed is:

1. An apparatus for controlling asymmetrical coasting of an endodontic reciprocating motor, the apparatus comprising:
    an endodontic motor capable of rotating a tool in a clockwise direction and in a counterclockwise direction, and
    a controller operatively coupled to the endodontic motor and capable of transmitting electronic signals to the endodontic motor to change the direction of rotation of the tool from the clockwise direction to the counterclockwise direction, controlling a forward coast time during which the endodontic motor coasts in the clockwise direction, and controlling a reverse coast time during which the endodontic motor coasts in the reverse direction, wherein the forward coast time is different from the reverse coast time.

2. The apparatus of claim 1 wherein the controller includes a processing unit operatively coupled to the endodontic motor and configured to direct the rotation of the endodontic motor in the forward direction for the forward coast time and configured to direct the rotation of the endodontic motor in the reverse direction for the reverse coast time.

3. The apparatus of claim 2 wherein the processing unit calculates the forward coast time separately from the reverse coast time.

4. The apparatus of claim 2 further comprising a plurality of user selectable modes including a clockwise rotation mode, a counterclockwise rotation mode, and a reciprocating mode, and wherein the processing unit calculates the forward coast time and the reverse coast time when the reciprocating mode is selected.

5. The apparatus of claim 2 wherein the processing unit is configured to determine a forward angular speed of the endodontic motor and to receive a forward coast setting and is configured to calculate the forward coast time based on a preset algorithm that includes the forward angular speed and the forward coast setting, and wherein the processing unit is configured to determine a reverse angular speed of the endodontic motor and to receive a reverse coast setting and is configured to calculate the reverse coast time based on a preset algorithm that includes the reverse angular speed and the reverse coast setting.

6. The apparatus of claim 5 wherein the preset algorithm for calculating the forward coast time is represented by the equation:

$$\text{forward coast time} = (-0.0005)(\text{forward angular speed}) + (0.08) + (0.0044)(\text{forward coast setting}).$$

7. The apparatus of claim 5 wherein the preset algorithm for calculating the reverse coast time is represented by the equation:

$$\text{reverse coast time} = (-0.0005)(\text{reverse angular speed}) + (0.08) + (0.0044)(\text{reverse coast setting}).$$

8. A method for asymmetrically coasting a reciprocating endodontic motor, comprising;
   rotating an endodontic motor in a forward direction;
   determining a forward coast time for the forward direction;
   coasting the endodontic motor in the forward direction for the determined forward coast time;
   after coasting the endodontic motor in the forward direction, rotating the endodontic motor in a reverse direction;
   determining a reverse coast time for the reverse direction separately from the determined forward coast time, the reverse coast time being different than the forward coast time; and
   coasting the endodontic motor in the reverse direction for the determined reverse coast time.

9. The method of claim 8 wherein, prior to determining the forward coast time, the method further comprises:
   selecting a forward coast setting and wherein determining the forward coast time includes calculating the forward coast time based on the forward coast setting.

10. The method of claim 8 wherein, prior to determining the reverse coast time, the method further comprises:
    selecting a reverse coast setting and wherein determining the reverse coast time includes calculating the reverse coast time based on the reverse coast setting.

11. The method of claim 8 wherein determining the forward coast time includes calculating the forward coast time based on a forward coast setting and a forward angular speed of the endodontic motor and wherein determining the reverse coast time includes calculating the reverse coast time based on a reverse coast setting and a reverse angular speed of the endodontic motor.

12. The method of claim 8 wherein after coasting the endodontic motor in the forward direction for the forward coast time and before rotating the endodontic motor in the reverse direction, the method further comprises:
    braking the motor to a stop.

13. The method of claim 8 wherein determining the forward coast time includes calculating the forward coast time by solving the equation:

$$\text{forward coast time} = (-0.0005)(\text{forward angular speed}) + (0.08) + (0.0044)(\text{forward coast setting}).$$

14. The method of claim 8 wherein determining the reverse coast time includes calculating the reverse coast time by solving the equation:

$$\text{reverse coast time} = (-0.0005)(\text{reverse angular speed}) + (0.08) + (0.0044)(\text{reverse coast setting}).$$

\* \* \* \* \*